United States Patent [19]

Luppi et al.

[11] Patent Number: 4,531,932

[45] Date of Patent: Jul. 30, 1985

[54] CENTRIFUGAL PLASMAPHERESIS DEVICE

[75] Inventors: Libero Luppi; Alessandro Calari, both of Mirandola, Italy

[73] Assignee: Dideco S.p.A., Mirandola, Italy

[21] Appl. No.: 443,975

[22] Filed: Nov. 22, 1982

[30] Foreign Application Priority Data

Nov. 27, 1981 [IT] Italy .............................. 25336 A/81
Jan. 20, 1982 [IT] Italy .............................. 19193 A/82

[51] Int. Cl.[3] .......................... A61M 5/00; B04B 5/02

[52] U.S. Cl. ........................................ 604/6; 210/927; 494/18; 494/13; 494/14; 494/21; 494/23

[58] Field of Search .................................... 494/17-18, 494/13-14, 21, 23; 210/927; 604/4-6; 128/DIG. 3

[56] References Cited

U.S. PATENT DOCUMENTS

| | | | |
|---|---|---|---|
| 3,993,560 | 11/1976 | Halpern | 604/4 |
| 4,010,894 | 3/1977 | Kellogg et al. | 210/927 |
| 4,098,456 | 7/1978 | Bayham | 494/17 |
| 4,146,172 | 3/1979 | Cullis et al. | 604/6 |
| 4,151,844 | 5/1979 | Cullis et al. | 604/6 |
| 4,256,696 | 3/1981 | Soodak | 494/13 |
| 4,402,680 | 9/1983 | Schoendorfer | 494/17 |
| 4,414,108 | 11/1983 | Ito | 210/927 |

FOREIGN PATENT DOCUMENTS

| | | | |
|---|---|---|---|
| 2002266 | 2/1979 | United Kingdom | 494/21 |

*Primary Examiner*—C. Fred Rosenbaum
*Assistant Examiner*—Gene B. Kartchner
*Attorney, Agent, or Firm*—Guido Modiano; Albert Josif

[57] ABSTRACT

The device comprises a single needle circuit having lines for admitting whole blood drawn from a patient to a continuously rotating rotor, re-introducing red cells and collecting plasma, the lines being respectively connected to the three outlets of a coupling static block rigidly attached to the rotor, two photocell-lightsource assemblies being further provided for automatically cyclically switching over the blood pick up and red cells introduction steps in the device steady state condition of operation.

9 Claims, 5 Drawing Figures

14
8a
2a
11a
8
2
11
15
16
17
18
18a
18b
19
20
20a
20b
21
22
22a
22b
23
24
24a
24b
25
25a
25b
2b
2c
8b
8c
11b
11c
III
1
2
3
4
5
6
7
9
9a
10
12
13

CENTRIFUGAL PLASMAPHERESIS DEVICE

BACKGROUND OF THE INVENTION

This invention relates to a device for plasmapheresis by centrifugation.

Several devices are known and commercially available which enable separation—called plasmapheresis—of plasma from red cells contained in the blood drawn from a donor or a patient in order to remove the plasma alone and re-introduce the red cells; with such prior devices, said separation is accomplished by centrifugating the blood, putting to use the different specific gravities of plasma and red cells, and it will be appreciated that of fundamental import is the dynamic balancing of the rotor which includes the ducting wherethrough blood is flown for undergoing centrifugation.

With some prior devices, this dynamic balance is obtained by suitably arranging counterweights at opposed positions to swellings in the ducts intended for accommodating the blood, but it will be appreciated that, if the system is balanced with all the ducts filled, it would not be so at the start of the operation, before the blood reaches it, unless said swellings are filled with physiological solution. This filling operation, which is inherently complicated because it involves preliminary removal of the air contained therein, represents a significant portion of the overall time duration of the operation, especially where this is performed on a donor, and is accordingly a highly disadvantageous feature of the devices.

Conventional devices, moreover, tend to be quite expensive owing to the complexity of their components, and generally unreliable in operation.

SUMMARY OF THE INVENTION

It is a primary object of this invention to provide a device for carrying out plasmapheresis by centrifugation which enables no-load starting, thus considerably shortening the operative times over conventional devices.

Another object of the invention is to provide a device of simple construction, thereby it can combine low cost with a high degree of reliability in operation.

According to one aspect of the present invention these objects are achieved by a centrifugation plasmapheresis device, a centrifugation plasmapheresis device comprising:

- a continuously rotating rotor for re-introducing red cells and collecting plasma in a provided vessel;
- a rotating hollow shaft supporting said rotating rotor;
- a single needle circuit having lines for admitting the whole blood drawn from a person to said continuously rotating rotor;
- a rotating block rigidly attached to said rotating rotor and having outlets arranged in radial symmetry;
- a static block supported by said rotating block and having outlets connected to said lines of said single needle circuit;
- at least two slots open at the top which are arranged in said rotating rotor;
- said slots having constantly varying radii with respect to the rotation axis of said rotating rotor;
- at least two pockets symmetrically housed in said two slots wherein centrifugation separation of red cells from plasma is to take place;
- said two pockets being formed from a collapsible flexible material;
- two tubes connected to one end of said pockets which is inserted in the smallest radius region of said slots;
- a small tube arranged along the entire circumference of the rotating rotor;
- two diametrically opposed fittings connected both with the other end of said pockets which is inserted in the largest radius region and with said small tube;
- two opposed radial channels extending substantially from the centerline of each of the semicircles of said small tube which are defined by said fittings connected to said outlets of said rotating block;
- automatically cyclically switching means for picking up the whole blood in a first step and for red cells re-introduction in a second step during steady state operation;
- attemperating temperature means arranged in said rotating rotor for preventing the blood from cooling during its residence in said rotating rotor with attendant viscosity increase which adversely effect the separation process, characterized in that it comprises a single needle circuit having lines for admitting whole blood drawn from a person to a continuously rotating rotor, re-introducing red cells, and collecting plasma in a specially provided vessel, said lines being respectively connected to the three outlets of the static block of a coupling comprising a rotating block rigidly attached to said rotor, said rotor being effective to radially support thereon at least those vessels wherein centrifugation separation of red cells from plasma is to take place, means being further provided for automatically cyclically switching over the whole blood pick up and red cell re-introduction steps during steady state operation of the device.

Advantageously, the connections of the vessels or containers wherein separation occurs of the red cells from plasma by centrifugation to the three outlets of the coupling rotating block will be also arranged in radial symmetry.

Again advantageously, the rotor may be provided, at least at an area adjoining the blood vessels, and formed from a good heat conductor material incorporating a plurality of heat-regulating plugs, so as to afford the best of conditions for the performance of the plasmapheresis process.

BRIEF DESCRIPTION OF THE DRAWINGS

Further features and advantages will be more apparent from the following description of some preferred but not limitative embodiments of the invention, as illustrated by way of example only in the accompanying drawings, where.

DESCRIPTION OF THE PREFERRED EMBODIMENTS

Figures 1, 2, 3:
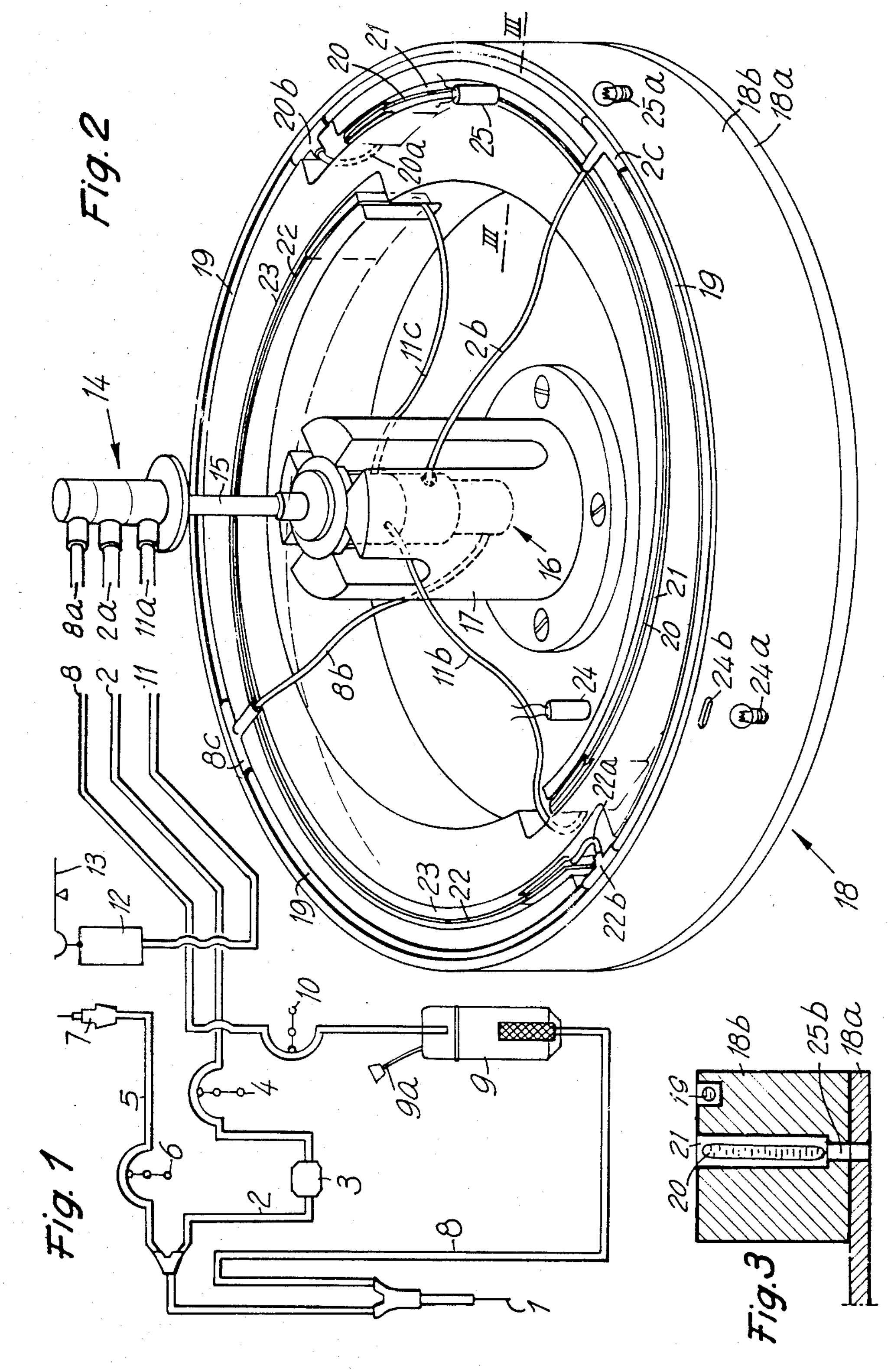
FIG. 1 is a diagramatic representation of the single needle circuit connected to the rotor.
FIG. 2 is a perspective view of the rotor, with parts shown in ghost outline.
FIG. 3 is a sectional view taken in the plane III—III of FIG. 2.

Making reference to the cited drawing FIGS. 1, 2, and 3, indicated at 1 is the connective needle with the donor or patient, whereto the whole blood pick up line 2 is connected which includes a low flow rate detector 3 and a peristaltic pump 4, and to which the line 5 is connected which has a peristaltic pump 6 constantly operating concurrently with the pump 4, which is conducted to the perforator 7, connected to an anticoagulant reservoir; to said needle 1 is also led a red cell re-introducting line 8 incorporating a dripper 9 which has a fitting 9*a* and peristaltic pump 10.

The diagram of FIG. 1 also shows a line 11 for transporting the plasma to the vessel 12, which has a scale 13 capable of emitting signals in a manner that will be explained hereinafter with reference to the device operation.

The three lines 2,8 and 11, cited hereinabove, are connected to three outlets of the static block 14 of the coupling, comprising, in a manner known per se, the connection 15 to the rotating block 16 formed with outlets matching those in the static block and being rigid with the support or holder 17 attached to the base plate 18*a* of the rotor, generally indicated at 18, which comprises additionally an annular element 18*b*.

More precisely, the whole blood pick up line 2 is connected to the outlet 2*a* of the static block 14, which matches, on the rotating block 16, with the outlet connected to a substantially radial channel 2*b* which is led to the fitting 2*c* provided on the small tube 19 which extends along the entire circumference of the rotor inserted in a specially provided groove. The red cell re-introducing line 8 is connected to the outlet 8*a* of the static block, to which there corresponds, on the rotating block, the outlet which is connected to the substantially radial channel 8*b*, extending in the same direction as the channel 2*b*, which is led to the fitting 8*c* provided on the small tube 19 at a position which is, therefore, diametrically opposed to that of the fitting 2*c*.

The plasma line 11 is connected to the outlet 11*a* of the static block, to which there corresponds on the rotating block the double outlet connected to the tubes 11*b* and 11*c* extending in the same direction.

The tube 11*b* reaches one end of the pocket 20, inserted through the slot indicated at 21 provided in the annular element 18*b* and shaped as a semicircle offcentered with respect to the rotation axis, and more specifically, the end inserted in the area closest to said rotation axis, while at the end inserted at the area farthest from the rotation axis, the channel 20*a* extends which is led to the fitting 20*b* on the small tube 19, at such a position as to divide the semicircle defined by the fittings 2*c* and 8*c* into two equal parts.

Similarly, the tube 11*c* is led to the closest end to the rotation axis of the pocket 22 which is inserted through the slot 23, identical to the slot 21, and spanning the opposed semicircle, while, from the other end of said pocket 22, there extends the small channel 22*a* which is led to the fitting 22*b* on the small tube 19 at such a location as to divide the other semicircle, defined by the fittings 2*c* and 8*c*, into two equal parts; it should be noted that said pockets 20 and 22 are formed from a flexible material adapted to collapse, thereby it affords advantageous conditions both at the start, for the withdrawal of air, and upon emptying, which operation may be effected in a complete manner.

The means of automating the cyclical switching over of the whole blood pick up and red cell re-introduction phases during the steady state operation comprises the two photocells 24 and 25 and related light sources 24*a* and 25*a*, arranged respectively above and below the rotor 18 and connected to the electric circuit actuating the peristaltic pumps 4 and 10, the former pump being located at a distance from the rotation axis which is equal to that of the through-going hole 24*b* provided at the bottom of the slot 21 in the proximities of the end close to said axis, the latter pump being located at a distance from the rotation axis which is equal to that of the through-going hole 25*b*, shown in FIG. 3, provided at the bottom of said slot 21 in the proximities of the end away from said axis.

The operation of this invention will be presently described.

At the beginning of an operation on a donor or patient, with the device inoperative throughout its parts and the re-introduction line 8 filled in a conventional manner with a physiological solution through the fitting 9*a*, said solution is caused, e.g. by manually operating the pump 10, to flood, by flowing in through 8*a*, the channel 8*b* and the semicircle of the small tube 19 included between the fittings 20*b* and 22*b*. At this point, the pump 4 on the whole blood pick up line is started, and by the time the blood, by flowing in through 2*a*, has flooded the channel 2*b* and the semicircle of the small tube 19 opposedly located to the one filled with physiological solution, the rotor 18 can be rotated because, from this time onwards, the system will be dynamically balanced, and it will remain so by virtue of the radial symmetry of all the components, throughout the operation, since the whole blood flows, through the channel tubes 20*a* and 22*a*, into the pockets 20 and 22 to gradually occupy constantly corresponding and diametrically opposed portions.

Within the pockets 20 and 22, which are provided with variable radii, and accordingly such as to subject the fluid contained therein to a differentiated centrifugal force in the various embodiments, there will occur separation of the red cells, which are heavier and hence liable to collect at the farthest regions of the pockets from the rotation axis, where centrifugal force is at a maximum, from the plasma which tends to move toward the closest region of the pockets to the rotation axis, whence it flows out through the tubes 11*b* and 11*c* to reach, through 11*a*, the line 11 which leads to the vessel 12. The first pick up phase just described ends upon the plasma-red cells interface reaching the hole 24*b* location, since this occurrence is sensed by the photocell 24, which controls the pump 4 to stop and the starting of the pump 10 on the line 8 of re-introduction of the red cells into the donor, while the rotor always keeps rotating. Consequently, the red cells will leave the pockets through the small channels 20*a* and 22*a* to re-enter, through the fittings 20*b* and 22*b*, that semicircle of the small tube 19 which contains the fitting 8*c*, being prevented from entering the other semicircle, which is shut off by the pump 4 being inoperative, and hence, through said fitting 8*c*, flow into the channel 8*b* and, after flowing past the coupling, into the re-introduction line 8; obviously, in this motion, the flow of red cells will entrain the separated plasma therealong, which plasma cannot be re-admixed because the rotor is still in operation, and the re-introduction step ends, at least for the first cycle and the directly following ones, while the amount of separated plasma is still small, at the time when the scale 13 senses that the vessel 12 has been completely emptied and stops the pump 10, at the same time controlling the start of a fresh pick up step.

After the first cycles, while the amount of separated plasma is higher than that corresponding to twice the volume included in the pocket 20 between the sections at the holes 24*b* and 25*b*, the end of the re-introductory phase or step is no longer controlled by the scale 13, but rather by the photocell 25 sensing the movement of the plasma-red cell interface past it; at this time, the pump 10 is stopped and the pump 4 restarted for a fresh pick up operation.

The steady state operation described above continues until the scale 13 shows filling of the vessel for the plasma 12, and, at this time, said vessel is clamped shut, the rotor is stopped, and, by means of the pump 10 on the re-introduction line, the donor or patient is returned all of the fluid present in the lines, which are of the disposable type, being quickly releasable from their seats in the rotor.

Figure 4:
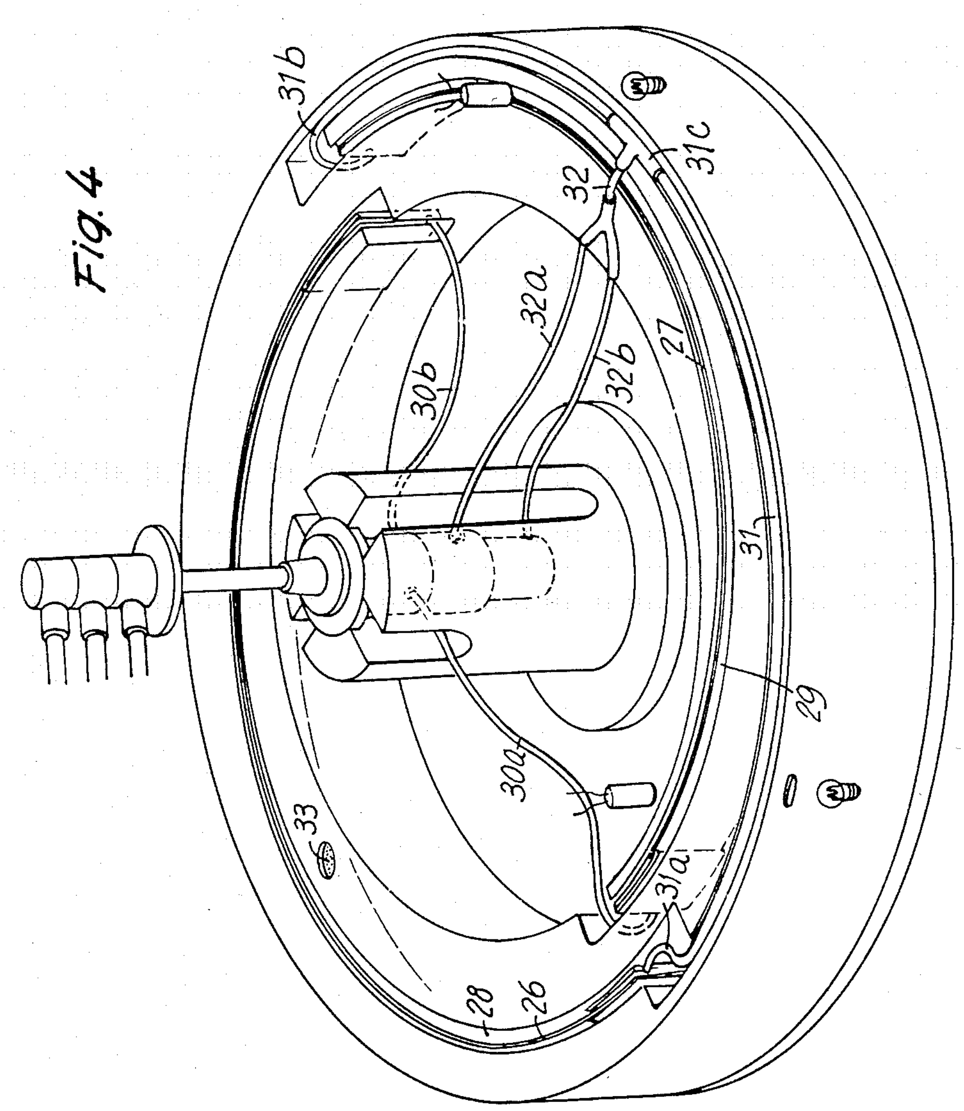
FIG. 4 is a perspective view of the rotor, according to a first modified embodiment thereof.

FIG. 4 illustrates a modified embodiment of the rotor of this invention. The two pockets 26 and 27 thereof, which are inserted through the slots 28 and 29, are connected, with their ends inserted in the smallest radius region, to the channel tubes 30*a* and 30*b* for plasma delivery, exactly as with the first embodiment described. However, differently from the foregoing, said pockets are here connected with the ends inserted in the largest radius region, at 31*a* and 31*b*, to the ends of the small tube 31 which spans a semicircle and has on its centerline the fitting 31*c* with the substantially radial channel 32 which is branched off in two channels, one of which, and precisely 32*a*, is connected with the outlet of the rotating block which corresponds to the outlet of the static block connected to the whole blood pick up line, whilst the other, indicated at 32*b*, is connected to that outlet which corresponds to the static block outlet connected to the red cell re-introduction line.

The small tube 31 and the channels 32,32*a* and 32*b* create, when filled with blood, a dynamic unbalance, however small, which is cancelled by the counterweight 33 located at a diametrically opposed location to the fitting 31*c*.

At the operation beginning, whole blood is admitted through 32*a* to fill the small tube 31, at which time, with the system balanced, the rotor is started to produce in the pockets the plasmapheresis described hereinabove. The operation automation is as described, and the re-introduction of the red cells takes place through the small tube 31 and channel 32*b*, since they cannot, on reaching the bifurcation of the channel 32, enter 32*a* which is shut off by the pump in the whole blood pick up line being inoperative.

Thus, a very simple, low cost device has been provided which can be started quite rapidly, since it is not necessary to perform any preliminary operations directed to establish a dynamic balance which is assured per se by the configuration of the device itself.

Figure 5:
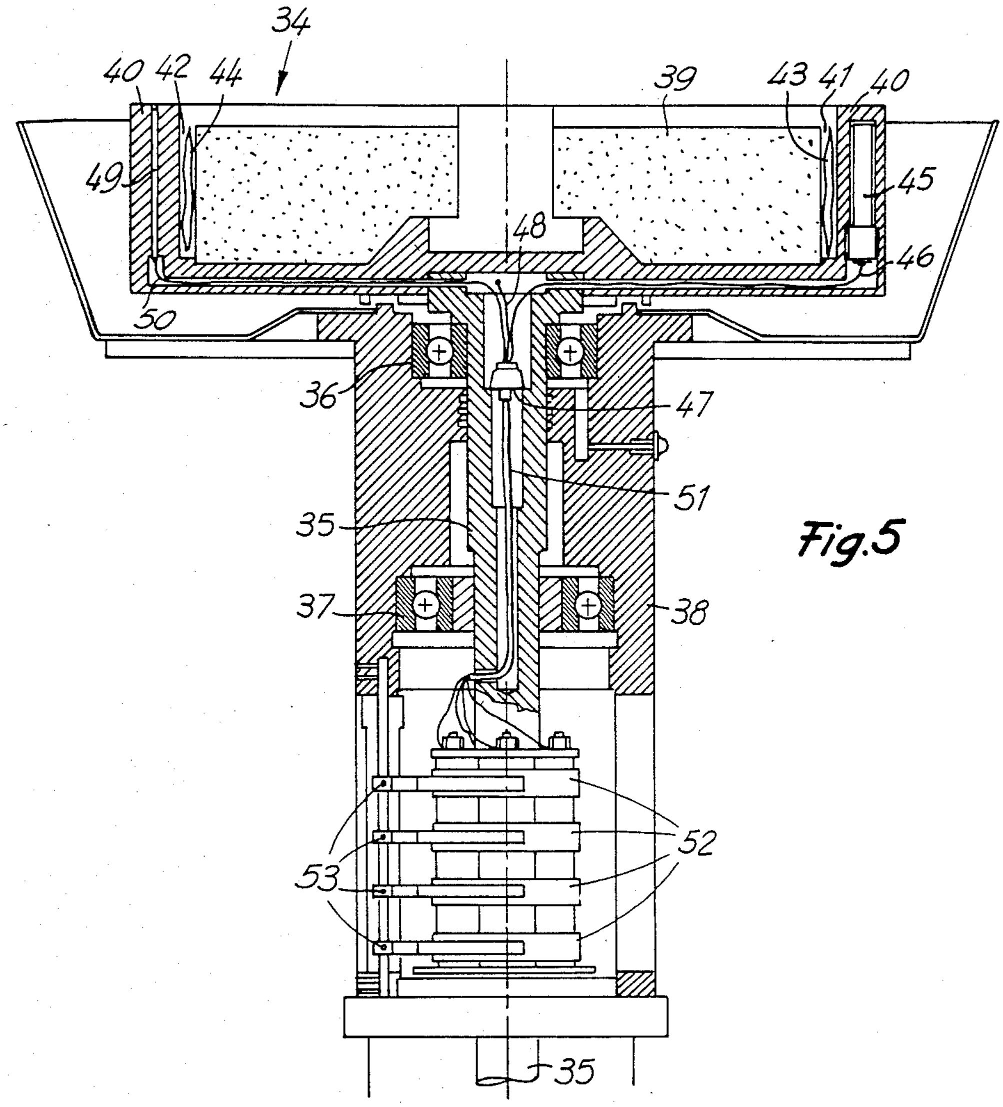
FIG. 5 is a sectional view taken in the plane containing the axis of rotation of a heat-regulated rotor.

To prevent the blood from cooling during its residence in the rotor and connective conduits, with attendant viscosity increase which would adversely affect the separation process, the rotor may be constructed as shown in FIG. 5.

Indicated generally at 34 in said Figure, is the rotor, which is carried on a hollow shaft 35 inserted, with the interposition of bearings 36 and 37, into the static body 38 of the machine, which is driven rotatively by a means not shown in the Figure.

Said rotor 34 is configured to fit the center block 39, formed from PVC and having an outer band 40 of a good heat conductor metal material, and between these elements slots 41 and 42 are formed which are adapted to enclose the pockets 43 and 44, wherein separation by centrifugation of red cells from plasma takes place. Provided on the band 40 are three heating plugs located at equal distances apart, one of which is shown in the Figure and indicated at 45; these plugs are electrically operated, and indicated at 46 is the lead connected to the plug 45, which is routed to the plug-socket pair 47 provided inside the hollow shaft 35, to which is also routed the lead indicated at 48 which is connected to another of said plugs.

The sensor element of the temperature control circuit comprises a platinum heating resistor 49, also connected electrically to the plug-socket pair 47 by means of the lead 50.

From said plug-socket 47, the electric leads extend through a common sleeve 51 to the rings 52, rigidly attached to the shaft 35 and conventionally contacting the brushes 53 effective to ensure electric continuity with the static portion of the machine, three of them being connected to the heating resistor 49 and one to the plugs, such as 45.

It will be apparent how with the arrangement just described it will be easy to automatically keep, according to the indications provided by the heating resistor 49, the band 40 at the temperature judged by the operator to be more suitable for a correct delivery of heat to the blood contained in the pockets 43 and 44, such that the blood can be maintained in optimum conditions for the separation process being carried out, thereby it will be possible to operate at low rpm and mitigate the danger of platelet depauperation.

The invention described in the foregoing is susceptible to many modifications and variations without departing from the scope of the instant inventive concept. Thus, as an example, the pocket accommodating slots could be given arcuate configurations and extend over different lengths from the semicircles described; moreover, the heating plugs may be provided in any desired number, and may also be replaced with Peltier effect cooling elements, where heat is to be removed.

Following the same outline given hereinabove, it is also possible to reach electrically the interior of the rotor for connecting actuators of any types, such as photocells.

In practicing the invention, all of the details may be replaced with other technically equivalent elements; furthermore, the materials used, and the shapes and dimensions, may be any selected ones to meet individual requirements.

I claim:

1. A centrifugation plasmapheresis device comprising:
   - a continuously rotating rotor for re-introducing red cells and collecting plasma in a provided vessel;
   - a rotating hollow shaft supporting said rotating rotor;
   - a single needle circuit having lines for admitting the whole blood drawn from a person to said continuously rotating rotor;
   - a rotating block rigidly attached to said rotating rotor and having outlets arranged in radial symmetry;
   - a static block supported by said rotating block and having outlets connected to said lines of said single needle circuit;

at least two slots symmetrically located and open at the top which are arranged in said rotating rotor;
said slots having constantly varying radii with respect to the rotation axis of said rotating rotor;
at least two pockets housed in said two slots wherein centrifugation separation of red cells from plasma is to take place;
said two pockets being formed from a collapsible flexible material;
two tubes one of each of said tubes connected to one end of each of said pockets which is inserted in the smallest radius region of said slots;
a small tube arranged along the entire circumference of the rotating rotor;
two diametrically opposed fittings each connected with an other end of said pockets which is inserted in the largest radius region and with said small tube, said fittings defining two semicircular portions of said small tube;
two opposed radial channels extending substantially from a centerline of each of said semicircles of said small tube which are defined by said fittings and connected to said outlets of said rotating block;
automatically cyclically switching means for picking up the whole blood in a first step and for red cells re-introduction in a second step during steady state operation;
attemperating temperature means arranged in said rotating rotor for preventing the blood from cooling during its residence in said rotating rotor with attendant viscosity increase which adversely effect the separation process.

2. A centrifugation plasmapheresis device as claimed in claim 1, wherein the device comprises four rotating rings engaging four fixed electric brushes to ensure electric continuity between said rotating rotor and a machine static portion, said rotating rings being rigidly attached to the hollow shaft.

3. A centrifugation plasmapheresis device as claimed in claim 1 wherein said attemperating temperature means comprise a plurality of heat regulating plugs for attemperating the temperature of a rotating rotor portion having a good heat conductor material, said heat regulating plugs being arranged in said portion at equal distance along said rotating rotor circumference.

4. A centrifugation plasmapheresis device as claimed in claim 1, wherein it comprises leads powering said heat regulating plugs, said leads being inserted through said hollow shaft and connected to one ring of the four rotating rings.

5. A centrifugation plasmapheresis device as claimed in claim 1 wherein the device comprises a sensor element regulating the temperature of said heat regulating plugs which is connected electrically to the other three rotating rings.

6. A centrifugation plasmapheresis device comprising:
a continuously rotating rotor for re-introducing red cells and collecting plasma in a provided vessel;
a rotating hollow shaft supporting said rotating rotor;
a single needle circuit having lines for admitting the whole blood drawn from a person to said continuously rotating rotor;
a rotating block rigidly attached to said rotating rotor and having outlets arranged in radial symmetry;
a static block supported by said rotating block and having outlets connected to said lines of said single needle circuit;
at least two slots symmetrically located and open at the top which are arranged in said rotating rotor;
said slots having constantly varying radii with respect to the rotation axis of said rotating rotor;
at least two pockets housed in said two slots wherein centrifugation separation of red cells from plasma is to take place;
said two pockets being formed from a collapsible flexible material;
two tubes one of each of said tubes connected to one end of each of said pockets which is inserted in the smallest radius region of said slots;
a small tube arranged along the entire circumference of the rotating rotor;
two diametrically opposed fittings each connected with an other end of said pockets which is inserted in the largest radius region and with said small tube, said fittings defining two semicircular portions of said small tube;
two opposed radial channels extending substantially from a centerline of each of said semicircles of said small tube which are defined by said fittings and connected to said outlets of said rotating block;
automatically cyclically switching means for picking up the whole blood in a first step and for red cells re-introduction in a second step during steady state operation;
a plurality of rotating rings rigidly attached to said hollow shaft;
a plurality of fixed electric brushes engaging said rotating rings to ensure electric continuity between said rotating rotor and a machine static portion;
a plurality of heat regulating plugs for attemperating the temperature of a rotating rotor portion having a good heat conductor material;
said heat regulating plugs being arranged at equal distances apart along said rotating rotor circumference;
leads powering said heat regulating plugs;
said leads being inserted through said hollow shaft and connected to one ring of the four rotating rings;
a sensor element regulating the temperature of said plugs which is connected electrically to the other three rotating rings.

7. A centrifugation plasmapheresis device as claimed in claim 6, wherein said automatically cyclically switching means comprise at least two photocells with respective light sources respectively overlying and underlying said rotating rotor, said photocells being connected to at least a peristaltic pumps arranged in said single needle circuit.

8. A centrifugation plasmapheresis device as claimed in claim 7, wherein said photocells are arranged at a distance from the rotation axis corresponding to that of each of two through-going holes provided at the bottom of one of the slots in the proximities of the ends thereof, so as to sense the movement past said holes of the red cell plasma and consequently control the switching over of first and second steps.

9. A centrifugation plasmapheresis device as claimed in claim 6 wherein said single needle circuit comprises a scale to sense the weight of the plasma vessel upon emptying of the same during the operation of re-introduction step for switching over from said re-introduction step to a pick up step.

* * * * *